United States Patent [19]
Patel et al.

[11] Patent Number: 5,647,052
[45] Date of Patent: Jul. 8, 1997

[54] VOLATILE SUBSTANCE DISPENSER AND METHOD OF DISPENSING A VOLATILE SUBSTANCE WITH DISSIPATION INDICATION

[75] Inventors: Manhar K. Patel, Saddle Brook; John M. Paulovich, Hewitt, both of N.J.

[73] Assignee: Reckitt & Colman Inc., Wayne, N.J.

[21] Appl. No.: 431,103

[22] Filed: Apr. 28, 1995

[51] Int. Cl.$^6$ .................................................. A61M 16/00
[52] U.S. Cl. ................................... 392/390; 392/393
[58] Field of Search ................................... 392/386–387, 392/390, 391, 393

[56] References Cited

U.S. PATENT DOCUMENTS

| | | |
|---|---|---|
| 1,230,342 | 6/1917 | Thornberg . |
| 1,547,160 | 7/1925 | Bailey . |
| 1,803,334 | 5/1931 | Lehmann . |
| 2,293,235 | 8/1942 | Zahner ........................ 219/45 |
| 2,714,649 | 8/1955 | Critzer ........................ 219/19 |
| 2,733,333 | 1/1956 | Peters ........................ 219/45 |
| 2,742,342 | 4/1956 | Dew et al. ........................ 21/53 |
| 2,931,880 | 4/1960 | Yaffe ........................ 392/390 |
| 2,942,090 | 6/1960 | Diehl ........................ 219/19 |
| 3,248,530 | 4/1966 | Titmas ........................ 240/2 |
| 3,780,260 | 12/1973 | Elsner ........................ 219/271 |
| 3,948,445 | 4/1976 | Andeweg ........................ 239/53 |
| 4,145,001 | 3/1979 | Weyenberg et al. ........................ 239/56 |
| 4,795,883 | 1/1989 | Glucksman et al. ........................ 392/390 |
| 4,849,606 | 7/1989 | Martins, III et al. ........................ 219/271 |
| 4,853,517 | 8/1989 | Bowen et al. ........................ 219/271 |
| 5,136,684 | 8/1992 | Lonker et al. ........................ 392/390 |
| 5,175,791 | 12/1992 | Muderlak et al. ........................ 392/390 |
| 5,220,636 | 6/1993 | Chang ........................ 392/392 |
| 5,230,837 | 7/1993 | Babasade ........................ 261/30 |

*Primary Examiner*—Teresa J. Walberg
*Assistant Examiner*—Sam Paik
*Attorney, Agent, or Firm*—Frederick H. Rabin

[57] ABSTRACT

A volatile substance dispenser is provided which provides an indication of the dissipation of a quantity of volatile substance by changing an electrical signal level after a time duration corresponding to an expected period time for the quantity of volatile substance to disseminate. A heat source causes the volatile substance to disseminate into the atmosphere. Dissipation of the volatile substance is indicated. For example, dissipation may be indicated by a light bulb burning out where the light bulb is a limited duration bulb with a lifetime that corresponds to the quantity of volatile substance. The dispenser may be disposable and may also serve as a night light.

19 Claims, 3 Drawing Sheets

FIG. 4
FIG. 5
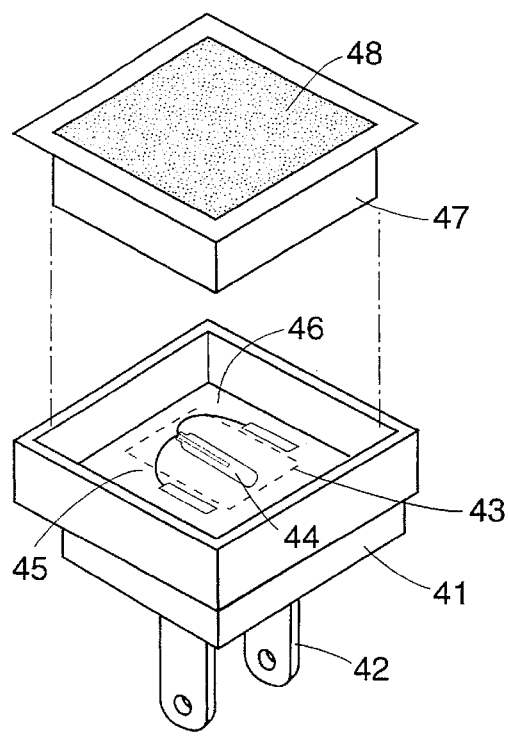
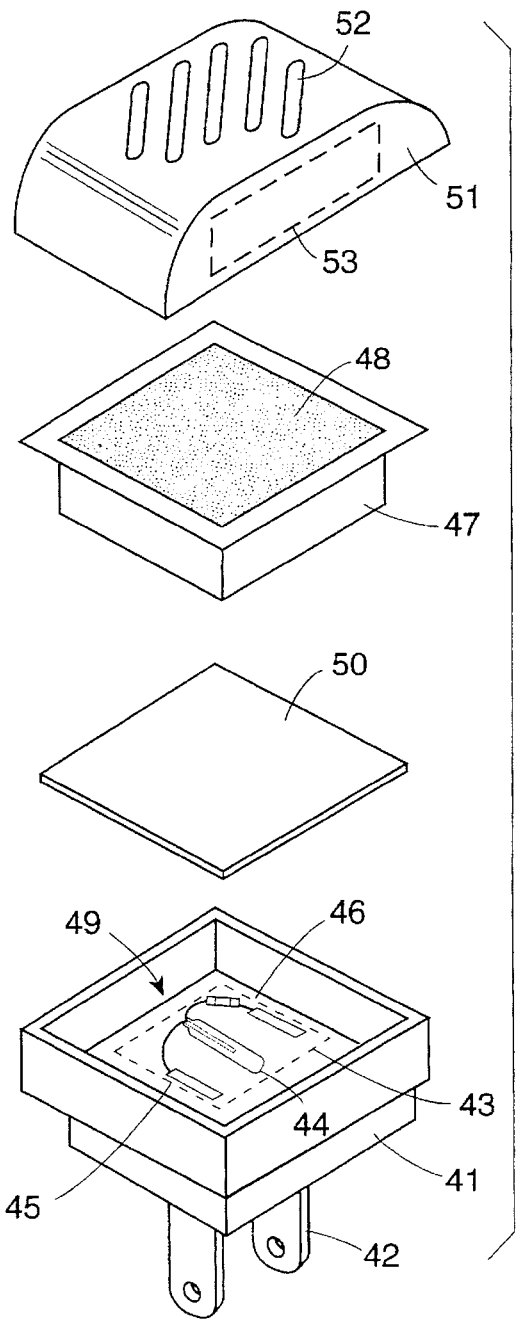

5,647,052

VOLATILE SUBSTANCE DISPENSER AND METHOD OF DISPENSING A VOLATILE SUBSTANCE WITH DISSIPATION INDICATION

FIELD OF THE INVENTION

This invention relates to a volatile substance dispenser and a method of dispensing a volatile substance. In particular, the invention relates to a dispenser providing controlled time release of a volatile substance with a heat source causing the volatile substance to dispense into the atmosphere in the form of a vapor.

BACKGROUND OF THE INVENTION

Dispensers for disseminating a volatile substance such as perfume, fragrance, incense, deodorant, disinfectant, medicated liquid, germicide, or insecticide have been known. These devices disguise, remove or create an odor or aroma. Andeweg, in U.S. Pat. No. 3,948,445 issued Apr. 6, 1976, discloses a combination air freshening device and night light. Andeweg's devices are illustrated in FIGS. 1, 2A, and 2B. As shown in FIG. 1, Andeweg's device has an electric plug base 1 with electric plug prongs 2 for inserting into a wall electrical receptacle or outlet. The base 1 mounts a light bulb 3 that is a source of both light and heat. Side walls 4, 5 and 6 are scent, air freshener and/or insecticide substance impregnated material walls subject to controlled release of vapor with the heating from light bulb 3. Andeweg also discloses the device of FIG. 2A which includes a base 11 with electric plug prongs 12 for plugging in a wall electrical receptacle or outlet and an electrical bulb socket into which the base of electric light bulb 13 is threaded. An open top container 14 of glass is held in place between the top of the base 11 and the base of the light bulb 13. A reservoir material 15 such as scented wax is placed in the cupped container 14. As shown in FIG. 2B Andeweg provides a device with a base 21 with electric plug prongs 22 and an electrical bulb socket into which the threaded base of electric light bulb 23 is threaded. A reservoir material 25 such as scented wax is placed between an outer container 24 and an inner container 26 above a spacer element 27.

A more recent development provides for a plug-in volatile substance dispenser as shown in FIGS. 3A and FIG. 3B. This dispenser has a base 31 with electric plug prongs 32 insertable into a wall electrical receptacle or outlet. Fuse links 34 distribute electricity to a screen printable film, fixed resistor heat pad 33 which is supplied with a thermal coating that encapsulates the electrical components and provides even heat distribution over the resistor heat pad 33. Alternatively, the resistor heat pad and thermal coating may be replaced with a chip resistor (not shown) with wires for connecting to the fuse link. A volatile substance is provided in absorbent substrate 35. Cover 36 has openings to permit the volatile substance to diffuse into the atmosphere. An impermeable film 37 covers the openings in cover 36 until the film is removed prior to use. In this dispenser, the resistor heat pad 33 or chip resistor is the source of heat for vaporizing the volatile substance.

It is known to view the volatile substance in a dispenser to determine if it is used up as in the Andeweg air freshener, discussed above and in Martens et al., U.S. Pat. No. 4,583,686 issued Apr. 22, 1986. Simply viewing the volatile substance to determine if it is used up is not possible if the volatile substance is impregnated in an absorbent material.

Elsner U.S. Pat. No. 3,780,260 issued Dec. 18, 1973, discloses a combination night light and liquid vaporizer wherein an electric lamp provides a heat source for vaporizing the liquid in the container as well as illumination for the night light. The lamp is controlled through an energizing circuit which includes an electric flow path through the vaporizable liquid between spaced electrodes built into the container. As soon as the level of the vaporizable liquid is reduced to an amount such that the circuit energizing the lamp is cut off, the lamp turns off. Hence, the Elsner night light and vaporizer detects the absence of the vaporizable liquid. The circuit, however, requiring a vaporizable liquid which permits electrical energy to flow between electrodes is rather complicated and not particularly reliable. The volatile substance must be a liquid.

There is, therefore, a need for a volatile substance dispenser and night light which provides an indication of the dissipation of the volatile substance without close inspection of the device to see if the volatile substance is gone or if a sufficient amount of the substance remains to be effective. Further, there is a need for a night light/volatile substance dispenser which is simple in construction and use and indicates the dissipation of the volatile substance if the substance is in a form such as impregnated in an absorbent material where dissipation cannot be readily determined by viewing the absorbent material. There is further a need for a night light/volatile substance dispenser which indicates dissipation of the volatile substance without complicated and unreliable detection of the volatile substance or unreliable circuit components such as electrodes. There is further a need for a night light/volatile substance dispenser which indicates the dissipation of the volatile substance although the volatile substance is not a liquid which permits electrical energy to flow through it.

SUMMARY OF THE INVENTION

It is an object of the invention to provide an improved combination night light and volatile substance dispenser which provides an indication of the dissipation of the volatile substance.

A further object of the invention is to provide a volatile substance dispenser which provides dissipation indication although the volatile substance is impregnated in an absorbent material and dissipation cannot be readily determined by viewing the volatile substance.

It is a further object of the invention to provide a volatile substance dispenser with dissipation indication which can be used for a volatile substance that is not a liquid which permits electric energy to flow through it.

It is a further object of the invention to provide a volatile substance dispenser with dissipation indication that does not require detection of the volatile substance.

It is still a further object of the invention to provide a volatile substance dispenser with dissipation indication that is simple in construction and hence inexpensive to manufacture.

Additionally, it is an object of the invention to provide a volatile substance dispenser with dissipation indication where a light bulb is used as the source of heat for vaporizing the volatile substance.

It is still another object of the invention to provide a volatile substance dispenser with dissipation indication which is disposable.

It is a further object of the invention to provide a volatile substance dispenser with dissipation indication employing a limited duration light bulb where the lifetime of the light bulb corresponds to the consumption of the volatile substance.

It is still a further object of the invention to provide a volatile substance dispenser with dissipation indication which can be used with a volatile substance in the form of a gel, solid or liquid.

These and other objects of the invention are accomplished by providing a volatile substance dispenser comprising a quantity of volatile substance; holding means for holding the quantity of volatile substance; a heat source, the heat source causing the volatile substance to disseminate into the atmosphere; and means for indicating dissipation of the quantity of volatile substance by changing an electrical signal level after a time duration corresponding to an expected period of time for the quantity of volatile substance to disseminate.

In a preferred embodiment, the volatile substance dispenser comprises a base portion for connecting to an electrical outlet; a quantity of volatile substance; holding means for holding the quantity of volatile substance on the base portion; a light bulb having an expected lifetime, the light bulb heating the volatile substance and causing the volatile substance to disseminate into the atmosphere in the form of vapor and the lifetime of the light bulb corresponding to the quantity of volatile substance so that dissipation of the quantity of volatile substance is indicated when the light bulb burns out.

The above and other objects, aspects, features and advantages of the invention will be more readily apparent from the description of the preferred embodiment thereof taken in conjunction with the accompanying drawings and appended claims.

BRIEF DESCRIPTION OF THE DRAWINGS

The invention is illustrated by way of example and not limitation in the figures of the accompanying drawings in which like references denote like or corresponding parts, and in which:

FIG. 4 is a perspective view of a volatile substance dispenser according to a first embodiment of the invention; and FIG. 5 is a perspective view of a volatile substance dispenser according to a second embodiment of the invention.

DESCRIPTION OF THE PREFERRED EMBODIMENTS

Figure 1:
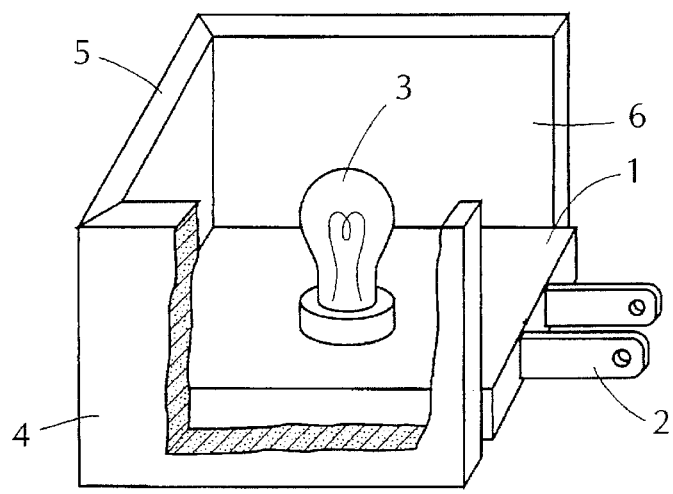
FIG. 1 is a partially broken away and sectioned perspective view of a volatile substance dispenser according to the prior art.
Figure 2:
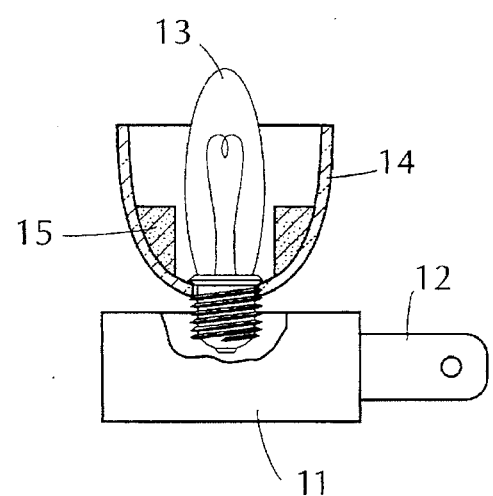
FIGS. 2A and 2B are volatile substance dispensers according to the prior art.
Figure 2B:
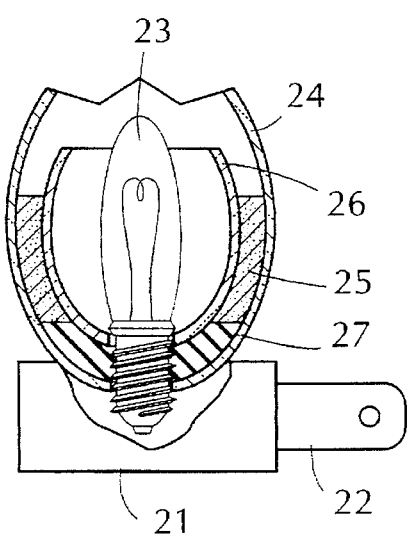
Figure 3A:
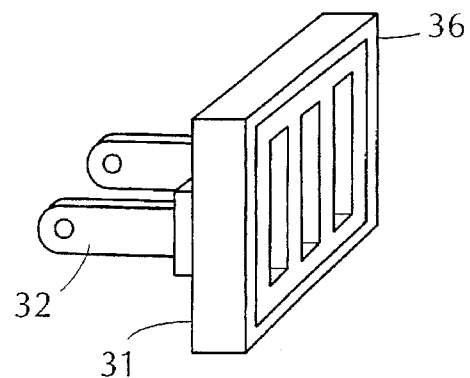
FIGS. 3A and 3B are perspective views of a volatile substance dispenser according to background art.
Figure 3B:
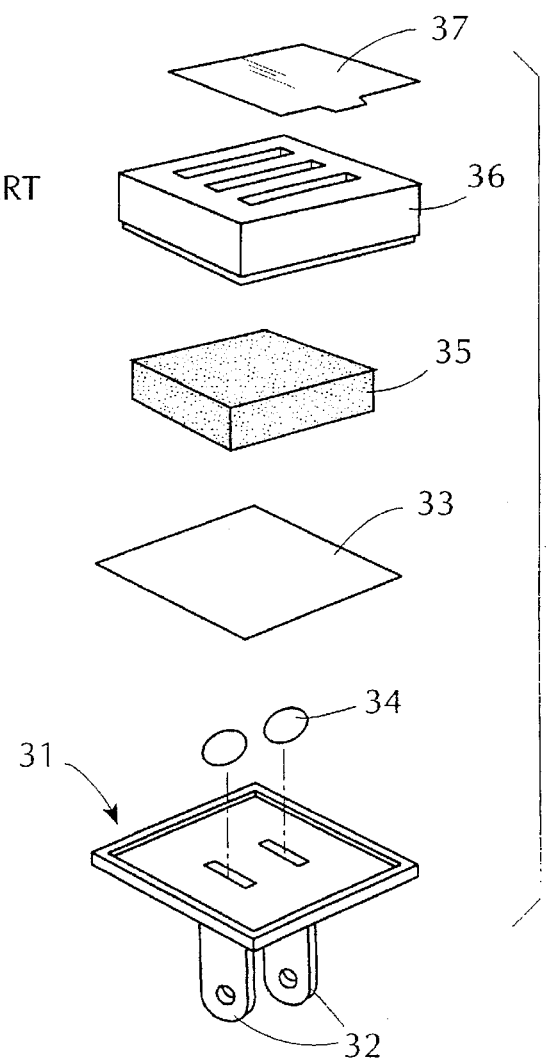

Referring to FIG. 4, a volatile substance dispenser is shown in accordance with the first embodiment of the invention.

The volatile substance dispenser of the first embodiment includes a base portion 41 with electric plug prongs 42 which are insertable into a wall electrical receptacle or outlet. The volatile substance dispenser includes electrical components illustrated by the dashed line 43. The electrical components include a heat source and indicator. The heat source vaporizes the volatile substance to disseminate the substance into the atmosphere in the form of vapor. The indicator indicates when the volatile substance is completely dissipated. As illustrated in the preferred embodiment of FIG. 4, the heat source and the indicator are both a light bulb 44. An electrical conductor 45 connects the electrical prongs 42 to the electrical components 43. The electrical conductor 45 can conduct an electrical signal with an electrical signal level. If discrete circuit elements are employed, the electrical signal level may be high or low. The electrical components are within a chamber 46 formed by the base portion 41 and side walls. The volatile substance dispenser further includes a holding means or tray 47 for holding a quantity of volatile substance 48.

In operation, the dissemination of the volatile substance 48 is activated when the o dispenser is plugged into an electrical receptacle or outlet. The electrical components 43, electrical prongs 42 and outlet form an electrical circuit. The heat source and indicator comprising a light bulb 44 heats the volatile substance so that it disseminates into the atmosphere in the form of a vapor. The light bulb 44 has a limited lifetime. The lifetime of the light bulb 44 corresponds to an expected period of time for the entire quantity of volatile substance 48 to disseminate. At the end of the lifetime of the light bulb, the light bulb burns out, breaking the electrical circuit. At that point an electrical signal level on electrical conductor 45 changes to zero (or low) and illumination stops. Since the lifetime or time duration of the light bulb corresponds to an expected period of time for the quantity of volatile substance to disseminate, dissipation is indicated when the light bulb burns out.

In the preferred embodiment as described in FIG. 4, the light bulb 44 is the means for indicating dissipation and an electrical signal on electrical conductor 45 is generated or is at a high level for the time duration or lifetime of the light bulb 44. When the light bulb 44 burns out, the electrical signal on electrical conductor 45 terminates or changes to a low level after the lifetime or the time duration of the light bulb. Alternatively, a means for indicating may be employed within the scope of the invention which generates an electrical signal or a high level signal after a time duration corresponding to an expected period of time for the quantity of volatile substance to disseminate. The indicating means may be a LED or other indicator. The indicating means may turn on after a time duration corresponding to the expected period of time for the quantity of volatile substance to disseminate.

In the preferred embodiment as shown in FIG. 4, the heat source is also the indicator or means for indicating. More particularly, the light bulb 44 is both the heat source for vaporizing the volatile substance and the means for indicating dissipation of the volatile substance upon terminating illumination. Within the scope of the invention, however, a separate heat source may be provided. The separate heat source may act alone or in combination with the indicator to vaporize the volatile substance. Also, the heat source may have a lifetime corresponding to the quantity of volatile substance. Further, the end of the lifetime of the heat source may be indicated.

In accordance with the preferred embodiment of the invention, the light bulb 44 radiates sufficient light to be used as a night light.

In a configuration where the light source or light bulb 44 is used as a night light the holding means or tray 47 is made so that it transmits light. Further, the volatile substance 48 as well as any material that it is impregnated in, transmits light. Additionally, the chamber 46 with side walls transmits light. The holding means or tray 47, volatile substance 48 and any material it is impregnated in, and chamber side walls may be transparent or translucent. Further, they may be made of various colors for a decorative effect.

With respect to the volatile substance 48, the substance may be in the form of a solid, liquid or gel. In the case of a solid volatile substance, the volatile substance may be in the form of a stick or a cake. The volatile substance may include a dilutant, stabilizing agents, preservatives, additives and fillers. Further, the substance may be retained in an absorbent material. The volatile substance may be retained in a porous absorbent substrate such as sintered polyethylene which is formed from porous granules of polyethylene which are pressed and formed by sintering into a shape. Alternatively, the porous absorbent substrate may be a polyethylene film or extruded film of cellulose acetate. Additionally, the absorbent substrate may be a polyolefin plastic material such as a microporous plastic film known as Teslin (Teslin is a registered trademark of PPG Industries, Inc.). Further, the volatile substance may be impregnated in an absorbent material such as a compressed paper fiber pad or a textile pad. The volatile substance may be a gel comprised of fragrance oil or other aromatic substance and fumed silica gel.

The dispenser of the present invention may be disposable and made of an inexpensive material like injection molded plastic such as polyethylene terephthalate. Alternatively, the dispenser may be made of metal, porcelain or glass. The dispenser may be refillable. When the dispenser is refillable, the entire holding means or tray 47 may be replaced.

The electrical prongs 42 are typical metal electrical prongs which when connected to an electrical outlet provide electricity to the heating source to vaporize the volatile substance and provide electricity to the indicator. Alternatively, the prongs may be plastic with metal inserts for conducting electrical current. The plastic prongs provide for increased safety. There are holes adjacent the prongs in the base portion 41 of the dispenser so that a conductor is run through the base portion 41 to provide electrical connections to the electrical components 43 of the dispenser.

The volatile substance dispenser may include an inner permeable or semi-permeable film or membrane layer which permits diffusion of vaporized volatile substance. The membrane layer may be of a material such as polyethylene. The membrane layer allows vapor to diffuse into the surrounding area over an extended period of time but retains the volatile substance in the holding means and deters tampering with and exposure to the volatile substance. Additionally, the volatile substance dispenser may include a vapor impermeable film or layer. When the volatile substance is to be dispensed from the dispenser, the vapor impermeable layer is peeled back or removed. A two layer package may be provided with an outer vapor impermeable layer and an inner vapor permeable layer. The outer vapor impermeable layer is peeled back leaving the inner vapor permeable membrane layer. The inner membrane layer retains the volatile substance in the holding means and prevents the user from contacting the substance while allowing vapor from the volatile substance to be released into the surroundings. The vapor impermeable layer may be an impermeable film such as aluminum foil or polypropylene.

FIG. 5 illustrates a second embodiment of the invention. Like reference numerals denote like or corresponding parts to those illustrated in FIG. 4. The volatile substance dispenser of FIG. 5 includes a resistor 49 in the electrical components indicated by the dashed line 43. The volatile substance dispenser further includes a cover plate 50 which may be transparent or translucent or colored for a decorative effect. If the dispenser is also a night light, the cover plate is manufactured to transmit light. The cover plate is secured onto the base portion 41 by a snap fit, sonic seal or glue. For a refillable dispenser, a snap fit is preferrably employed. The dispenser shown in FIG. 5 further includes a cover 51. The cover 51 may be decorative and may be transparent or translucent to transmit light for a dispenser which is also a night light. The cover 51 has openings 52 in the upper surface to permit diffusion of vaporized volatile substance. The cover 51 may also include openings 53 in the side walls to permit refilling the holding means or tray 47. The cover 51 is secured onto the base portion 41 by a snap fit, sonic seal or glue with the holding means or tray 47 sandwiched between the cover 51 and the cover plate 50. For a refillable dispenser, a snap fit may be preferred.

Just as with the other elements of the dispenser, the cover 51 and cover plate 50 may be manufactured of injection molded plastic, glass, porcelain, or metal.

As discussed above, the holding means or tray 47 may have a film membrane layer sealed on the edge. An inner vapor permeable membrane or film layer may be exposed by peeling away an outer vapor impermeable membrane or film layer.

The entire structure may be manufactured to transmit light if the dispenser is also to be employed as a night light. The volatile substance dispenser of the present invention is safe and employs low voltages. A low wattage incandescent light bulb is employed soldered to the base portion 41. A 2–4 watt light bulb is employed. The light bulb has a limited life of about 1000 hours which approximates the expected period of time for the quantity of volatile substance 48 to disseminate into the surroundings. Hence, the invention provides a plug-in volatile substance dispenser which is activated upon being plugged in. Further, the dispenser permits controlled even release of the volatile substance by a self contained source of heat. Dissipation of the volatile substance is indicated. Further the dispenser can be disposable.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

We claim:

1. A volatile substance dispenser comprising:
   a. a quantity of volatile substance;
   b. holding means for holding said quantity of volatile substance;
   c. a heat source, said heat source causing said volatile substance to disseminate into the atmosphere and constituting an electrical signal for a time duration corresponding approximately to an expected period of time for the quantity of volatile substance to dissipate.

2. The volatile substance dispenser according to claim 1, wherein said heat source has a lifetime corresponding to the quantity of said volatile substance.

3. The volatile substance dispenser according to claim 2, wherein the end of the lifetime of said heat source is indicated.

4. The volatile substance dispenser according to claim 3, wherein said heat source is a light bulb and the end of the lifetime of said heat source is indicated when the light bulb burns out.

5. The volatile substance dispenser according to claim 1, further comprising a base portion for connecting to an electrical outlet.

6. The volatile substance dispenser according to claim 4, wherein the light bulb functions as a night light.

7. The volatile substance dispenser according to claim 4, wherein said holding means transmits light.

8. The volatile substance dispenser according to claim 7, wherein said volatile substance transmits light.

9. The volatile substance dispenser according to claim 4, further comprising a chamber for said light bulb which chamber transmits light.

10. The volatile substance dispenser according to claim 1, wherein said volatile substance is in the form of a solid.

11. The volatile substance dispenser according to claim 1, wherein said volatile substance is in the form of a liquid.

12. The volatile substance dispenser according to claim 11, wherein said liquid volatile substance is retained in an absorbent material.

13. The volatile substance dispenser according to claim 1, wherein said volatile substance is in the form of a gel.

14. The volatile substance dispenser according to claim 1, wherein said holding means is refillable.

15. The volatile substance dispenser according to claim 1, wherein said dispenser is disposable.

16. A volatile substance dispenser, comprising:

a. a base portion for connecting to an electrical outlet;

b. a quantity of volatile substance;

c. holding means for holding said quantity of volatile substance on said base portion; and d. a light bulb having an expected lifetime, said light bulb heating said volatile substance and causing said volatile substance to disseminate into the atmosphere in the form of vapor and said lifetime of said light bulb corresponding approximately to the quantity of volatile substance so that dissipation of said quantity of volatile substance is indicated when said light bulb burns out.

17. A method of dispensing a volatile substance comprising the steps of:

providing a quantity of volatile substance; and providing a light bulb to heat said volatile substance, said light bulb having an expected lifetime that corresponds approximately to said quantity of volatile substance, so that said light bulb burns out when said quantity of volatile substance is dissipated.

18. The method according to claim 17, further comprising the steps of: refilling said quantity of volatile substance; and replacing said light bulb with another light bulb with an expected lifetime corresponding approximately to said refilled quantity of volatile substance.

19. The method according to claim 17, wherein said light bulb radiates enough light to be used as a light source.

* * * * *